United States Patent [19]
Roth et al.

[11] Patent Number: 5,207,672
[45] Date of Patent: May 4, 1993

[54] INSTRUMENT AND METHOD FOR INTRALUMINALLY RELIEVING STENOSIS

[75] Inventors: Robert A. Roth, Brookline; Michael A. Martinelli, Winchester, both of Mass.

[73] Assignee: Intra-Sonix, Inc., Burlington, Mass.

[21] Appl. No.: 641,457

[22] Filed: Jan. 14, 1991

Related U.S. Application Data

[63] Continuation-in-part of Ser. No. 346,790, May 3, 1989, abandoned.

[51] Int. Cl.$^5$ .......................... A61N 5/06; A61B 8/12
[52] U.S. Cl. ......................................... 606/10; 606/7; 606/12; 128/398; 128/660.03
[58] Field of Search ............ 328/395, 392, 398, 660.1, 328/660.3, 660.5; 606/2-7, 10-19; 604/20

[56] References Cited

U.S. PATENT DOCUMENTS

| | | | |
|---|---|---|---|
| 4,445,892 | 5/1984 | Hussein et al. | 606/18 |
| 4,672,963 | 6/1987 | Barker | 606/12 |
| 4,779,624 | 10/1988 | Yokoi | 128/660.03 |
| 4,887,605 | 12/1989 | Angelsen et al. | 606/18 |

FOREIGN PATENT DOCUMENTS

| | | | |
|---|---|---|---|
| 63-74108 | 5/1988 | Japan . | |
| 83/03188 | 9/1983 | World Int. Prop. O. | 606/15 |

OTHER PUBLICATIONS

"Use of Gas Jet Appositional Pressurization in Endoscopic Laser Photocoagulation" by Kimura et al IEEE Transactions on Biomed. Eng. vol. BME-25 No. 3 May 1978.

*Primary Examiner*—David M. Shay
*Attorney, Agent, or Firm*—Schiller & Kusmer

[57] ABSTRACT

An instrument for and method of effectively treating the prostatic urethra so as to relieve the symptoms associated with an enlarged urethra is disclosed. The tissue of at least selected portions of the prostate are compressed (preferably with a balloon inserted into the prostatic urethra so as to enhance hemostasis) and at least selected portions of the compressed tissue are directly irradiated (preferably with a laser beam transmitted from within the passageway in selected radial directions and moved along the prostatic urethra while exposing the tissue) so as to cause coagulation necrosis of selected portions of the compressed tissue so that as the tissue heals, the necrosed tissue slowly sloughs off during normal urination through the urinary tract so as to effectively remove the constricted portions of the prostatic urethra. Ultrasonic transducers are used from within the prostatic urethra to image the tissue as it is irradiated so as to monitor the procedure to insure proper exposure to the laser beam.

17 Claims, 8 Drawing Sheets

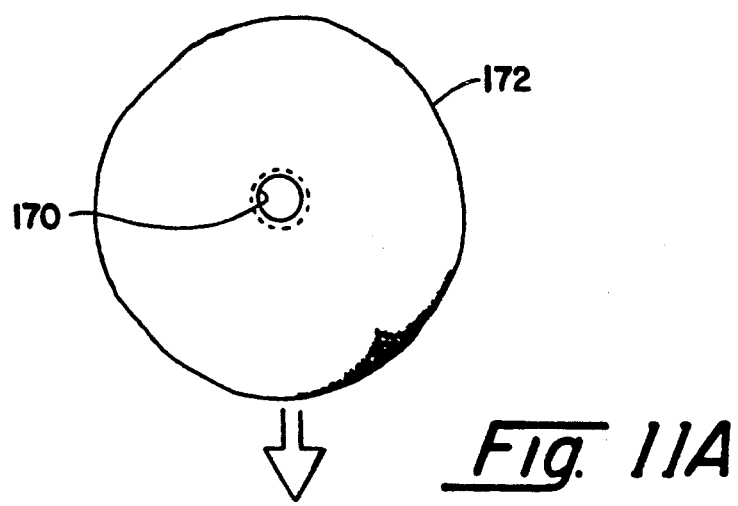
Fig. 11A
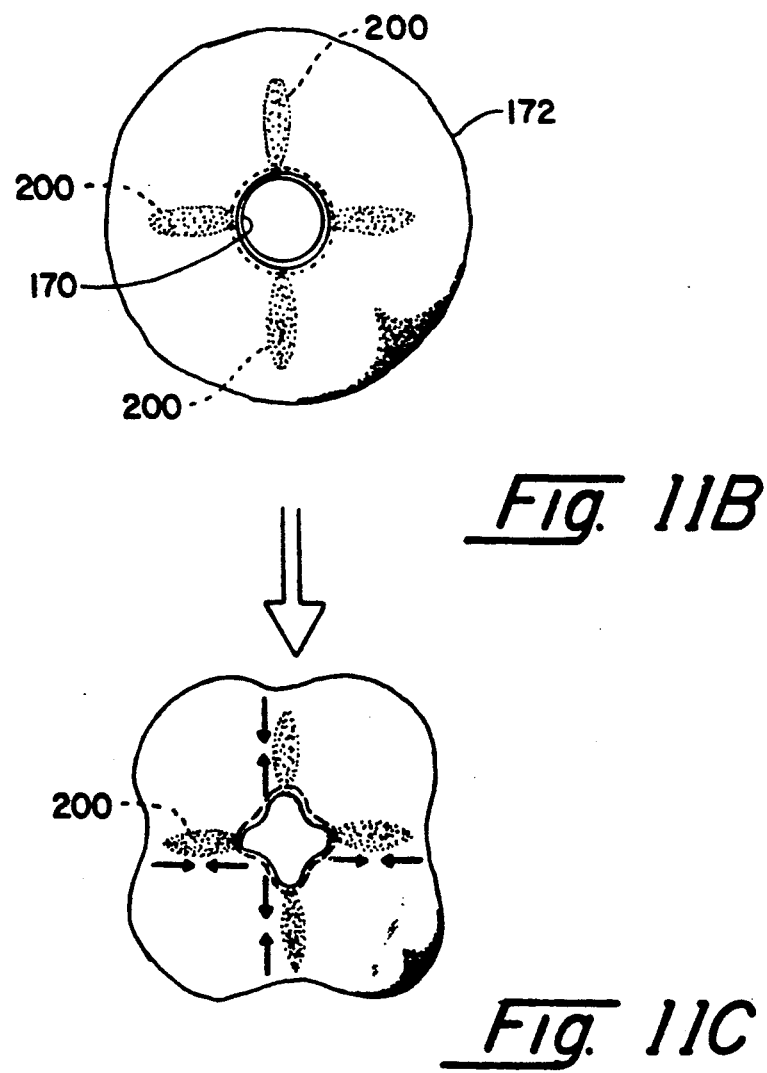
Fig. 11B
Fig. 11C

INSTRUMENT AND METHOD FOR INTRALUMINALLY RELIEVING STENOSIS

COPENDING APPLICATIONS

This application is a continuation-in-part of U.S. patent application Ser. No. 346,790 filed May 3, 1989, now abandoned.

BACKGROUND OF THE INVENTION

The present invention relates generally to intraluminal surgery, and more particularly to an improved instrument for and technique of transluminally opening any constricted regions of a passageway through a portion of a living body, and in particular, the prostatic urethra of an enlarged prostate.

As is generally well known the prostate is located at the base of the bladder, where it surrounds a portion of the urethra, the tube connecting the bladder to the outside world. The function of the . prostate is to produce a fluid which becomes a part of the ejaculated semen (which is also carried through the urethra). As men grow older, the tissue of the prostate often begins to enlarge, a condition called hyperplasia. As the bulk of the prostate enlarges, the gland begins to constrict the portion of the urethra passing through the prostate and thus prevent the normal flow of urine, a condition known as benign prostatic hypertrophy or hyperplasia (BPH). As BPH develops, one or more constricted or stenotic regions within the prostatic urethra can from time to time obstruct the flow of urine; so the signs of BPH are difficulty starting urination, dribbling following urination, reduced force of the stream of urine, a tendency to urinate frequently in small amounts as well as pain and discomfort. As a result an increase in urinary tract infections can occur. The symptoms are common; 75%-80% of men over the age of fifty are affected. See, for example, the *Harvard Medical Health Letter:* September 1988; Volume 13; Number 11; pages 114 4 and Castaneda, Flavio et al.; "Prostatic Urethra: Experimental Dilation in Dogs"; *Radiology:* June, 1987; pp. 645-648. In fact recent statistics apparently reveal that a 50 year old man has a 20-25% chance of undergoing treatment for this condition during his lifetime. See Castaneda et al., supra. It is currently estimated that about 500,000 prostatectomies (the most common method of treatment), are performed each year in the United States alone. See Castaneda, Flavio et al.; "Benign Prostatic Hypertrophy: Retrograde Transurethral Dilation of the Prostatic Urethra in Humans" *Radiology;* June, 1987, pp. 649-653.

When the obstructive symptoms of BPH become bothersome, the constricted portions of the urethra are usually reopened surgically. Current accepted treatment for BPH involves either open or transurethral surgery, which is costly and is associated with an acceptable but undesirable degree of mortality (estimated from 1.3% to 3.2%—see Castaneda, Flavio et al.; "Benign Prostatic Hypertrophy: Retrograde Transurethral Dilation of the Prostatic Urethra in Humans" *Radiology;* June, 1987, pp. 649-653) and With a significant degree of morbidity, especially in less fit patients.

The most common surgical procedure for BPH, as an alternative to open surgery, is a transurethral resection of the prostate, or TURP. The transurethral resection involves inserting a resectoscope through the urethra. A spring wire, adapted to carry an electric current, is inserted through the resectoscope for use in removing tissue. The wire carries one current for cutting away "chips" of tissue with the resectoscope and another current for cauterizing the remaining tissue to minimize bleeding. As much as two cubic inches of tissue are removed in this way.

The TURP surgical technique is not trivial nor inexpensive, though the actual procedure can ordinarily be done within one hour. The procedure carries similar risks as many of those associated with other general surgical procedures, including those associated with the use of general anesthesia. In addition, intraoperative irrigation fluids are required to flush blood from the prostatic urethra while tissue is being removed creating a danger that the flushing fluid will enter the blood circulatory system through iatrogenic openings into veins causing fluid overload and possible death, a result known as "post-TURP" syndrome. Other surgical hazards include stricture formation at the urethra or bladder neck, post-manipulation pain or bladder spasm, urinary tract infections, and reactive urethral swelling which can cause urinary obstruction and epididymitis. Other complications include retrograde ejaculation and delayed recurrent obstruction of the bladder neck area. Further, the post-operative care following a TURP procedure requires a prolonged hospital stay, creating substantial costs for medical care. The appropriate DRG (Diagnostically Related Group), currently designated by Medicare, for the TURP procedure presently entails an average length of hospital stay of 5.8 days. For a discussion of current pressures to reduce allowable Medicare fees for the TURP procedure and the impact of such reduced fees on urological patient care and the American urologist, see Holtgrewe, H. L. et al.; "Transurethral Prostatectomy: Practice Aspects of the Dominant Operation in American Urology"; *The Journal of Urology:* volume 141 (*1989*); pp. *248-253*. In addition, some men have reported sexual dysfunction following the resection. Certain men have also become incontinent as a result of the surgery because of inadvertent damage done to the external sphincter muscles positioned at the apex of the prostate for controlling urine flow. The surgery usually results in moderate discomfort with some post-operative bleeding being usual.

As a result of the trauma that many men experience from TURP and the relatively long in-patient care required for post operative recovery, alternative techniques of treating BPH are being investigated. For example, using hormonal treatments to prevent or reverse prostate enlargement has long been considered in the treatment of prostate enlargement. Male hormones are known to promote growth of the gland. However, there have been some uncertainties about the role played by hormones in creating BPH. Other devices for treatment of the prostate utilize heat, as for example a device sold by Armonite, Inc. of New York. The latter device provides thermal therapy to the prostate transrectally by radiating the prostate with microwave heat which is claimed to result in the shrinkage of the affected prostate tissue. The long term results of such therapy are currently inconclusive.

Methods of injecting medications directly into the prostate through a catheter extending into the prostatic urethra have been attempted. However, these injections are frequently ineffective due both to the poor absorption of such medications by the prostate, as well as to the difficulty inherent in positioning and retaining the catheter with respect to the affected area, and generally result in reoccurring prostatic disorders. An example of a device for positioning such a catheter and injecting medications into the prostate is shown in U.S. Pat. No. 3,977,408 issued to MacKew.

Another approach to treating BPH is a technique known as transurethral balloon dilation of the prostate. In this approach a catheter having an inflatable balloon positioned on the distal end of the catheter is transurethrally inserted into the portion of the urethra extending through the prostate. The balloon is then inflated so that the expanding balloon dilates the urethra and is held in its inflated state for a limited period of time, e.g., between ten and sixty minutes. See, for example, Castaneda, et al.; "Prostatic Urethra: Experimental Dilation in Dogs"; *Radiology;* June, 1987, pp. 645-648; and Castaneda, et al.; "Benign Prostatic Hypertrophy: Retrograde Transurethral Dilation of the Prostatic Urethra in Humans" *Radiology:* June, 1987, pp. 649-653. See also U.S. Pat. No. 4,660,560 issued to Lester Klein. The balloon described in the last mentioned Castaneda et al. article is inflated at a pressure of between 3 and 6 atmospheres and held under pressure for about ten minutes. During the balloon dilation procedure the tissue of the urethra must be expanded beyond its normal elastic limit otherwise the urethra will not remain dilated for very long. Accordingly, the balloon is sized to expand, for example, to a 25 mm diameter so as to cause the tissue within the averaged sized urethra to stretch to the point of actually tearing or cracking so that when the tissue heals, permanent fissures will remain so that the urethra will remain dilated. But even expanding the tissue just beyond the elastic limits does not necessarily insure long term effects on relieving the stenosis and constriction of the urethral walls due to the nature of the resilient muscle tissues and large bulk of the hypertrophied prostate which has a tendency to rebound after temporary compression. See U.S. Pat. No. 4,762,128 issued to Rosenbluth. Accordingly, the latter patentee proposes to insert a stent in the prostatic urethra after being dilated by the balloon and removing the stent at a later time. The problem with inserted stents is that they are difficult to remove once they are inserted and there is a tendency for irritation and encrustation.

The use of laser radiation has been described for acutely (intraoperatively) removing tissue of the prostate gland by ablation (vaporization) so as to remove tumors or all or part of the gland as an alternative to the electrocautery resection technique described above. See U.S. Pat. No. 4,672,963 issued to Dr. Israel Barken and Smith, Jr., Joseph A. et al.; "Laser Photoradiation in Urologic Surgery"; *The Journal of Urology:* Vol. 31, April, 1984, pp. 631-635, cited therein. However, use of a laser to acutely remove tissue from the prostate by ablation would not necessarily reduce post-operative bleeding and trauma, impotence and incontinence. This problem of using laser energy to remove prostatic tissue relates to the manner in which laser energy is applied. Specifically, in order to remove tissue acutely the laser energy is applied through a fiber with the tip of the fiber positioned transurethrally essentially directly in contact with the prostate tissue. Direct contact with the tip of a fiber transmitting laser energy causes tissue to quickly reach 100° C., wherein the tissue water vaporizes creating steam and an explosion, referred to as the "popcorn" effect. This method of tissue destruction is also poorly controlled and inefficient for removal of substantial amounts of tissue. For one, the tip of the laser fiber can become covered with charred tissue and require frequent cleaning. In addition, characteristics of the tissue itself, such as the amount of adenoma versus the amount of stroma, and the amount of blood within the tissue affect overall laser action. For example, blood at the tissue surface at the prostatic urethra highly absorbs Nd:YAG laser energy, causes superficial charring (carbonization), and, therefore, reduces tissue penetration by the laser, whereas blood flow beneath the tissue surface conducts heat away from the tissue and requires longer exposure time before the tissue will exceed 100° C. and be ablated.

The device described in U.S. Pat. No. 4,672,963 uses a computer to continuously adjust the amount of laser radiation transmitted to the prostate during the procedure. Accordingly, the device includes an ultrasonic probe, inserted transrectally or positioned externally, for imaging the prostate in real time during the procedure so as to provide real time data regarding the destruction of the prostate tissue so as to enable the computer to adjust the laser radiation accordingly. Transrectal and external ultrasonic imaging of the prostate are well known as further suggested by Sanders, R. C. et al., "Update on Prostatic Ultrasound", *Urologic Radiology* 1987; Fleischer, Arthur C., "Prostatic Endosonography—A Potential Screening Test"; *Diagnostic Imaging.* April 1987, pp. 78-82; and Lee, Fred, "Prostatic Evaluation by Transrectal Sonography: Criteria for Diagnosis of Early Carcinoma", *Radiology.* Vol. 158, pp 91-95, January, 1986.

Other uses of a laser for removing constrictions of a stenotic region of upper air passageways by vaporizing tissue with a laser beam to form radial cuts in the stenotic region of the air passageways has been suggested—see Shapshay et al.; "Endoscopic Treatment of Subglottic and Tracheal Stenosis by Radial Laser Incision and Dilation"; *Annals of Otology, Rhinology & Laryngology:* Vol. 96, No. 6, November-December 1987, pp. 661-664.

OBJECTS AND SUMMARY OF THE INVENTION

It is a general object of the present invention to provide an improved instrument for and technique of relieving the constrictive conditions of a constricted passageway of a body part in a manner that reduces or substantially eliminates the above-noted problems.

Another object of the present invention is to provide an improved instrument for and technique of relieving the symptoms of BPH while substantially reducing the length and degree of post-operative care.

And another object of the present invention is to provide an improved instrument for and technique of relieving the symptoms of BPH while reducing or substantially eliminating the threat of post-TURP syndrome and post-operative bleeding and trauma, impotence and incontinence associated with current TURP and other resection procedures.

Yet another object of the present invention is to provide an improved instrument and technique of relieving the symptoms of prostate enlargement without the need of hormonal treatments or long term heat therapy.

Still another object of the present invention is to provide an improved instrument for and technique of causing coagulation necrosis of selective portions of the prostate, with minimal ablation (vaporization), so that the necrosed tissue slowly sloughs off over time with the normal passage of urine through the prostate so as to increase, post operatively, the internal diameter of the prostatic urethra.

And yet another object of the present invention is to provide an improved instrument for and technique of compressing at least selected portions of a prostate preferably within the elastic limit of the tissue so as to improve hemostasis and so that selected tissue of the compressed portions can be subsequently irradiated with laser energy so as to cause coagulation necrosis of those portions of the prostate so treated and effectively increase the post operative internal cross-sectional diameter of the prostatic urethra.

And still another object of the present invention is to provide an improved instrument and technique which allows for more predictable laser penetration into prostatic tissue by reducing the flow of blood and other fluids through the surface tissue of the prostatic urethra and providing non-contact exposure of laser radiation at a constant distance to the surface tissue along the path of the prostatic urethra so as to maximize coagulation necrosis and minimize acute (intraoperative) removal of the tissue.

And still another object of the present invention is to provide an improved instrument and technique which allows the user to view, intraluminally, selective tissue, in real time during an operative procedure for dilating the passageway so as to insure selective laser exposure of portions of the tissue surrounding the lumen and avoid exposure to sensitive anatomy.

And yet another object of the present invention is to achieve the foregoing objects with a surgical technique and instrument for generally treating, intraluminally, any stenotic regions within the lumen of a living body so as to post-operatively effectively open such regions.

These and other objects of the present invention are achieved by an instrument for and method of effectively opening a passageway through a portion of a body part so as to relieve the symptoms from constrictions within the passageway. In accordance with the present invention, selected portions of the tissue of the body are exposed to laser radiation so as to cause coagulation necrosis by thermal absorption with minimal or no ablation (vaporization) of the tissue. Such necrosed tissue tends to slowly slough off, without significant bleeding so as to post operatively effectively eliminate the stenonic regions, and open the passageway. As will be more evident hereinafter, the procedure performed with the instrument of the present invention induces general necrosis with the intent for the necrosed tissue to be removed by normal body processes (in the case of the prostatic urethra through urination). In this context the process is capable of producing a general coagulation necrosis and by normal body processes removal of the treated tissue, without actual excision or vaporization of the tissue so as to distinguish the process from those describe, for example, in European Patent Application 85402067.4 of Dr. Richard J. Spears, published May 28, 1986 under Publication number 0182689 and U.S. Pat. No. 4,799,479 issued to Dr. Spears (in which an inflated balloon is used in a primary modality to remodel the opening in an artery by cracking the plaque as the balloon is expanded and trapping blood within the fissures of the plaque, and then using radiant heat produced by a heating element which in turn is heated by a laser [or alternatively, heating the plaque directly with the laser beam], to heat the trapped blood so as to fuse the plaque and thereby eliminate the elastic recoil of the normal constituents of the vessel wall so as to create a "biostent", which is clearly not inducing general necrosis in the connective tissue of the vessel wall such that any of the connective tissue or the plaque will slough off into the bloodstream, a result clearly posing a danger to the patient), or in the Shapshay et al. article, supra (where the tissue is excised by vaporization).

Preferably, in accordance with the present invention, the tissue of at least selected portions of the body part are compressed (preferably with a balloon inserted into the passageway) so as to compress blood vessels of the body part forming the passageway in order to improve hemostasis and thus improve the laser beam penetration. At least selected portions of the compressed tissue are exposed to laser energy (preferably with a laser beam transmitted from within the passageway in selected radial directions) so as to cause general necrosis of the tissue, so that the necrotic tissue slowly sloughs off over time so as to effectively open the natural passageway. Compressing the tissue so as to reduce blood flow therethrough prior to direct laser energy exposure has the additional benefit of allowing for more uniform and deeper absorption of the laser energy by the affected tissue. Ultrasonic transducers are preferably used from within the passageway to image the tissue as it is exposed to and heated by the laser energy so as to monitor the procedure to insure proper exposure to the laser beam, the intensity and direction of which is controlled by the surgeon.

Other objects of the invention will in part be obvious and will in part appear hereinafter. The invention accordingly comprises the processes involving the several steps and the relation and order of one or more of such steps with respect to each of the others, and the apparatus possessing the construction, combination of elements, and arrangement of parts exemplified in the following detailed disclosure, and the scope of the application of which will be indicated in the claims.

BRIEF DESCRIPTION OF THE INVENTION

For a fuller understanding of the nature and objects of the present invention, reference should be had to the following detailed description taken in connection with the accompanying drawings wherein.

Figure 10:
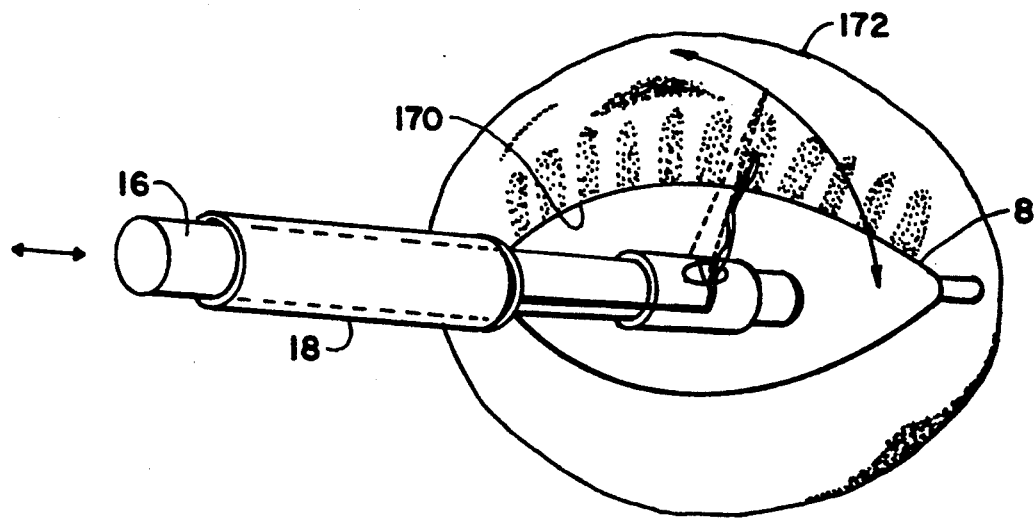

FIG. 10 is an anatomical illustration showing the catheter unit in place and selected tissue exposed to laser radiation so as to cause general necrosis of the tissue; and FIGS. 11A, 11B and 11C are anatomical cross-sectional views through a prostate generally normal to the elongated direction of the prostatic urethra for illustrating the effective dilation of the prostatic urethra as a result of the procedures described herein.

DETAILED DESCRIPTION OF THE INVENTION

Generally, in accordance with the method of the present invention a unique surgical procedure is provided which is generally useful in effectively dilating a stenotic region in a passageway through a part of a living body, and in particular, useful in relieving the symptoms of BPH. The procedure is preferably carried out using the instrument of the present invention. Generally, the instrument preferably includes means for transluminally delivering laser radiation at a power level and for a duration so as to cause general necrosis of selected portions of the living body so that as the necrotic tissue sloughs off the previously constricted passageway is effectively opened. The instrument preferably includes means for compressing the targeted tissue and associated blood vessels so as to enhance hemostasis and allow for uniform and more predictable absorption of laser energy. The preferred system and method described herein is particularly adapted for relieving the symptoms of BPH by effectively eliminating any stenotic regions of the prostate. Sufficient compression can be placed on the prostate gland with an inflatable, substantially non-compliant, flexible balloon, from within the prostatic urethra out, so as to achieve the desired results without exceeding the elastic limit of the tissue. The preferred instrument further includes means for transurethrally ultrasonically viewing at least a portion of the prostate tissue so that the portions of the prostate to be irradiated can be selected by the user, and the selected tissue exposed to the laser radiation can be observed and monitored by the user in real time during the procedure. This observation is particularly facilitated by the fact that dehydrated tissue becomes somewhat echogenic, i.e., visible by ultrasound imaging. This aspect is particularly significant since dehydration occurs at a temperature between about 100° C. at the transition from the coagulation necrosis regime to the ablation regime so that ultrasonic viewing can be used to minimize or prevent the latter regime.

Figure 1:
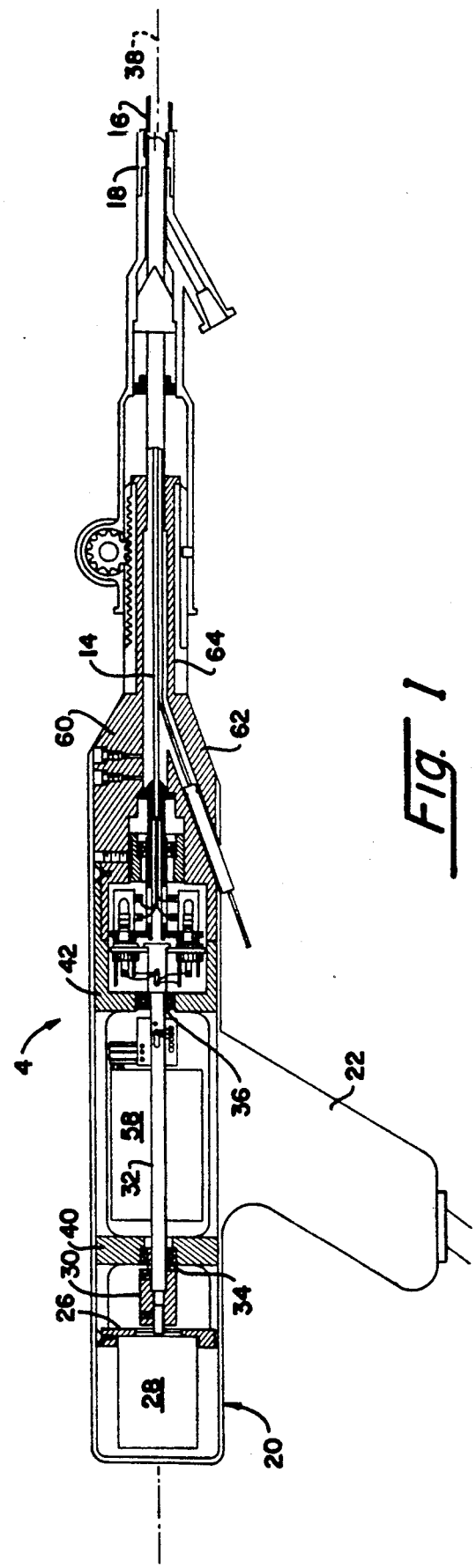
FIG. 1 is a cross-sectional side view of the control unit of the preferred embodiment of the present invention.
Figure 2:
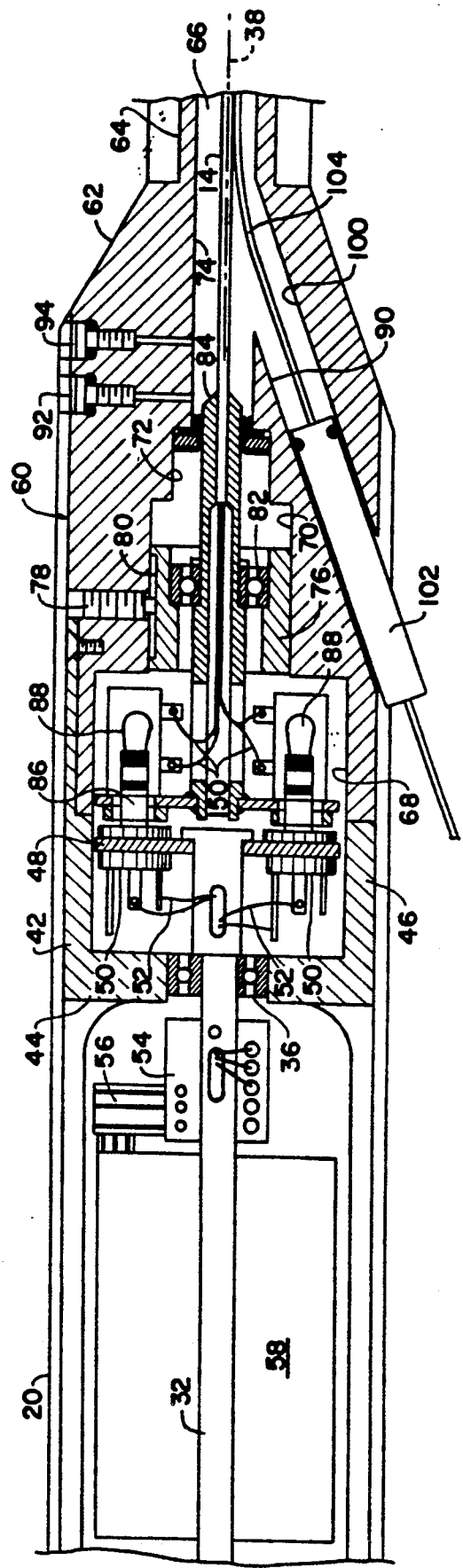
FIG. 2 is an enlarged cross-sectional side view of a portion of the control unit shown in FIG. 1.
Figure 3:
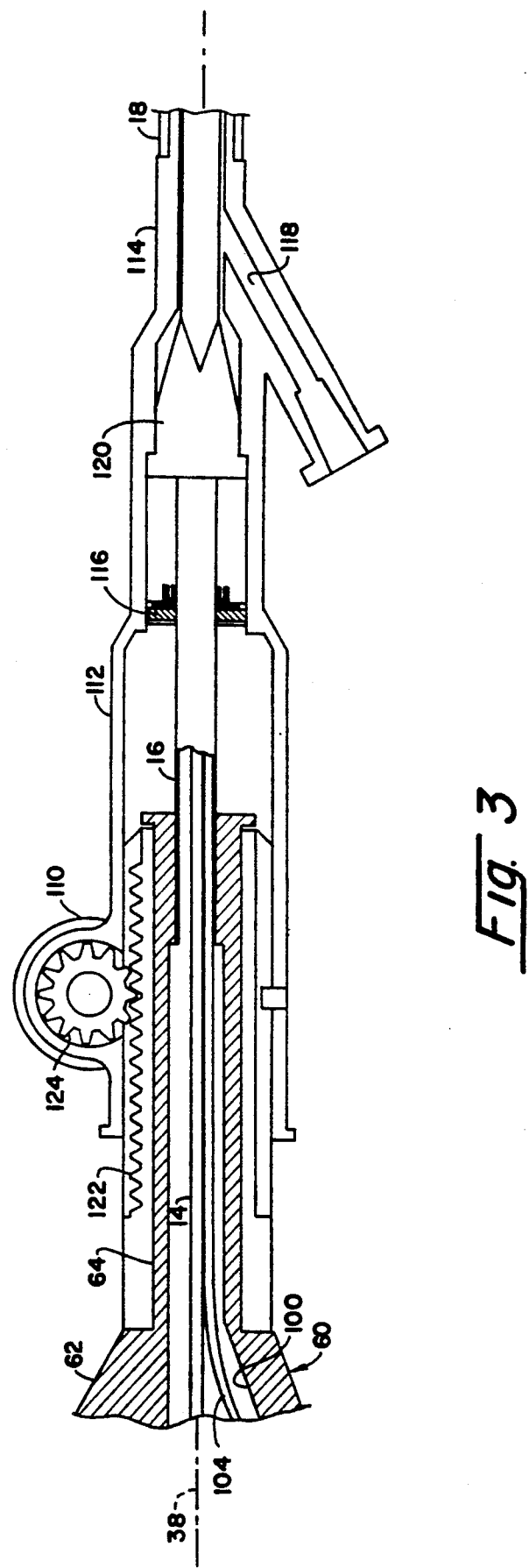
FIG. 3 is an enlarged cross-sectional side view of another portion of the control unit shown in FIG. 1.
Figure 4:
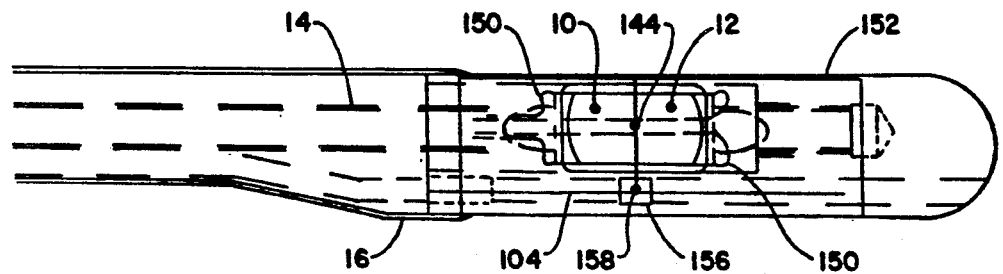
FIG. 4 is a top view of the remote end portion of the transducer and laser probe forming a part of the preferred catheter unit of the present invention.
Figure 5:
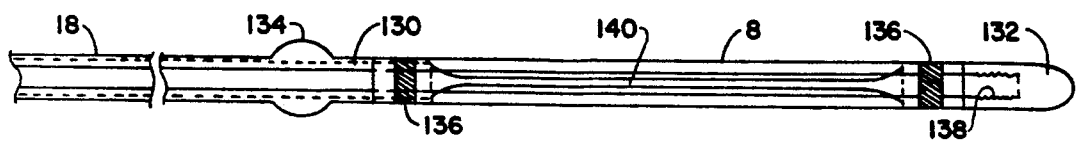
FIG. 5 is a cross-sectional side view of the remote end portion of the catheter casing of the preferred catheter unit of the present invention provided with a stylet so that the casing can be inserted into the prostatic urethra.
Figure 6:
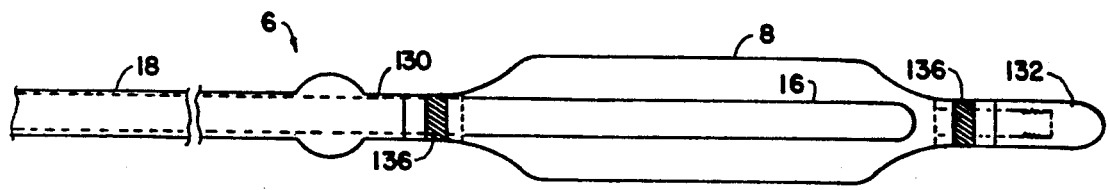
FIG. 6 is the same cross-sectional side view of the remote end portion of the catheter with the balloon inflated and the transducer and laser probe positioned in place with the casing of the catheter unit.

Referring to FIGS. 1-6 the instrument of the present invention generally comprises a control unit 4 (whose detail is shown in FIGS. 1-3), and catheter unit 6 (whose detail is shown in FIGS. 4-6). The catheter unit 6 is adapted to cooperate with the control unit 4 so that the user can carry out the procedure.

As described in greater detail hereinafter, the catheter unit generally includes an inflatable substantially non-compliant balloon 8, disposed at the remote end of the catheter unit, for temporarily opening at least a portion of the prostatic urethra and sized so as to compress at least the surface tissue of the prostatic urethra of an averaged sized prostate gland enlarged by BPH.

The catheter unit also includes means for transmitting a laser beam along an axis transverse (preferably perpendicular) to the general direction of the urethra so that the laser beam can be selectively directed into portions of the tissue compressed by the balloon 8. The amount of laser radiation is sufficient to cause coagulation necrosis of the exposed tissue in the direction of the laser beam axis. In fact, as will be more evident hereinafter, with the balloon compressing the tissue to promote hemostasis, improved direct laser penetration of the tissue is achieved. With a substantial restriction of blood flow into the surface tissue of the prostatic urethra, and the laser beam emitted at a constant distance from the point of emission of the device directly into the tissue surface, deeper penetration and more predictable laser irradiation is achieved. As described generally in Fisher, J. C., "Basic Laser Physics and Interaction of Laser Light with Soft Tissue," from *Endoscopic Laser Surgery Handbook*, edited by S. M. Shapshay, New York: Marcel Dekker Inc., pp. 1-130, at p. 122, 1987, when soft tissue of the type which readily conducts thermal energy from a 40 watt beam of a Nd:YAG laser is irradiated by such a laser, scattering in the tissue causes the illuminated volume to be much larger in diameter than the effective diameter of the laser beam, and about 8 mm deep. The isothermal boundary at 60° C. grows larger with time after the onset of irradiation as heat is conducted through the tissue. The point of maximum histological power density is on the beam axis below the tissue surface and can be the nucleus of a popcorn explosion with prolonged irradiation. As the tissue heals, the necrosed tissue will slough off, without significant bleeding, with normal passage of urine through the urinary tract, so as to effectively increase the post-operative internal opening through the prostatic urethra and thus increase urinary flow. Finally, as illustrated in FIG. 4, the catheter unit 6 preferably includes an ultrasound transmitter and receiver, 10 and 12, mounted on a shaft 14 and extending through and sealed within sleeve 16, which in turn, as best shown in FIG. 6, is positioned and axially movable within an outer casing 18 which forms the outer sleeve of the catheter unit. The casing 18 is sized for the average urethra, with about 7 mm diameter (22F) being typical.

The ultrasound transmitter 10 and receiver 12 provide real time imaging while the catheter unit is in place within the prostatic urethra, so that the specific areas to be exposed to laser radiation can be easily selected and monitored while exposed to the laser radiation. Ultrasonic imaging provides a distinct advantage over direct optical viewing as used for the TURP procedure since most of the tissue damage illuminated by the laser energy is below the surface of the prostatic urethra which would be out of view of a direct viewing optical instrument, and as mentioned above, dehydrated tissue is somewhat echogenic so that tissue ablation can be minimized. The foregoing will be described in greater detail and become more apparent hereinafter.

More specifically, the control unit 4 is shown in greater detail in FIGS. 1-3. The control unit 4 comprises a housing 20 including a hand grip 22, although the grip may be omitted if desired. The housing includes a hollow rear cylindrical portion 24 for receiving a mounting plate 26 for supporting the scanning motor 28. The scanning motor includes means for sensing the angular position of the rotor of the motor (not shown in FIGS. 1-3, but indicated in FIG. 7 as shaft encoder 168 and described hereinafter). The rotor shaft of the motor 28 is connected through the motor coupling 30 to the drive shaft 32, which in turn is positioned in the two bearing assemblies 34 and 36, respectively supported in supports 40 and 42, so as to be rotatable about the axis of rotation 38. As shown in greater detail in FIG. 2, support 42 is preferably cylindrically-shaped and includes the radially extending portion 44 for supporting the bearing assembly 36 and the axial extending cylindrical wall portion 46 secured to the wall of the housing 20. A connector assembly 48 is secured to the end of and adapted to rotate with the shaft 32. Assembly 48 includes at least two electrical connectors 50 which are suitably wired with leads 52. The latter are threaded through a hollow portion of the shaft 32 to an electrical anchor 54, which in turn is connected to the flex cable 56. Flex cable 56, in turn, is connected to the printed circuit assembly board 58 which carries the various electronic components required to operate the units 4 and 6.

As shown in FIG. 2, an assembly 60 is suitably secured to the cylindrical wall portion 46 of the support 42 and includes a main body portion 62 and an elongated end portion 64 (best shown in FIG. 3). An elongated hollow passageway 66 extends the entire axial length of the assembly 60 coaxial with axis 38. The passageway 66 is provided with at least four sections 68, 70, 72 and 74. The first section 68 is provided in the proximal end of the main body portion 62 of the assembly 60 and is of a relatively large diameter. The intermediate section 70 of the passageway is of an intermediate diameter, while the third section 72 is of a yet smaller diameter. The fourth section 74 of passageway 66 is provided at the opposite remote end of the elongated end portion 64 and is of a relatively small diameter. A hollow adjusting sleeve 76 is shown disposed in the second section 70 of passageway 66 and is axially adjustable along the axis 38. A set screw 78 extends through the wall of the body portion 62 and engages an axially extending groove 80 formed in the outer surface of the sleeve 76 so as to fix the sleeve in place. Sleeve 76 supports the bearing assembly 82. A hollow inner sleeve 84 is rotatably supported within the bearing assembly 82. A second connector assembly 86 is secured to the end of the inner sleeve 84 opposite the connector assembly 48 and is adapted to rotate with the sleeve about the axis 38. Assembly 86 includes a pair of electrical connectors 88 connected to and adapted to rotate with the electrical connectors 50 of the assembly 48 about the axis 38. The shaft 14 is secured within the inner sleeve 84 so as to rotate with the sleeve. As will be more evident hereafter, wires 150 extending through the shaft 14 from the ultrasound transmitter and receiver 10 and 12 are connected to the connectors 88 so as to connect the transmitter and receiver to the assembly board 58.

The end of the inner sleeve 84 is mounted in an oil seal 90, secured within the third section 72 of the passageway 66 and sealing the third section from the second section 70. Fill and vent ports 92 and 94 are provided in the wall of main body portion 62 of the nozzle assembly 60 for filling and emptying oil into the third section of the passageway which fills the third and fourth portions 72 and 74 of the passageway 66 and the spaces between the shaft 14 and the sleeve 16 of the catheter unit 6, as will be more evident hereinafter.

Again referring to FIG. 2, a laser fiber port 100 is provided in the main body portion 62 of the assembly 60 for receiving a laser fiber connector 102. The connector 102 is connected to laser fibers 104 applied on or extending through the "probe" formed by shaft 14 and sleeve 16 to the remote end of the probe shown best in FIG. 4 and described hereinafter. The connector 102 is adapted to be connected to a laser beam delivery system as described in greater detail hereinafter.

As shown in FIG. 3, the sleeve 16 is secured at one end to the end of the elongated end portion 64 of the nozzle assembly 60 with any suitable means so as to hermetically seal the two together and allow oil inserted into the fill port 92 to flow into spaces provided between the shaft 14 and sleeve 16.

A linear adjustment assembly 110 is used to connect the control unit 4 with the catheter unit 6. Assembly 110 is coaxially mounted on the elongated end portion 64 of the nozzle assembly 60. Assembly 110 includes an outer tubular housing 112 mounted on the elongated end portion 64 of the nozzle assembly 60 coaxial with the axis 38. Housing 112 is hermetically secured at its remote end at 114 to the outer casing 18 of the catheter unit 6 so that fluid can be introduced between outer casing and the sleeve 16 of the catheter unit. Accordingly, a fluid seal 116 is used to mount the sleeve 16 within the housing 112 so as to seal the remote end portion of the housing and the spaces between the outer casing 18 and sleeve 16 from the remainder of the housing 112. Further, a fluid port 118 is provided between the seal 116 and the remote end of the assembly 110 for introducing a fluid into the spaces between the casing 18 and sleeve 16. The fluid used to inflate the balloon is transparent to both the laser beam and ultrasound transmitted through the fluid. The fluid will depend on the particular application of the device. For most applications an inert liquid such as water is chosen so that in the event of rupture of the balloon the liquid will not effect the tissue to which the water is exposed.

A duck bill valve 120 is provided between the port 118 and the seal 116 so that the control unit 4, shaft 14 and sleeve 16 can be inserted and withdrawn from the linear adjustment assembly and the casing 18, while substantially maintaining the fluid pressure within the casing as for example when the balloon 8 is inflated. Assembly 110 also includes a rack and pinion gear assembly 122, 124, with the rack gear 122 secured to the outer surface of the elongated end portion 64 of the assembly 60 and the pinion gear 124 secured to the housing 112 so that rotation of the pinion gear 124 moves the shaft 14 and sleeve 16 (axially fixed to the nozzle assembly) relative to the outer casing 18 along the longitudinal axis of the catheter unit, defined by axis 38, for reasons which will become more evident hereinafter.

Referring to FIGS. 4–6, the catheter unit 6 will be described in greater detail. As shown best in FIGS. 5 and 6, the balloon 8 is open at both ends. One end of the balloon is secured to the remote end 130 of the casing 18 of the unit 6 so as to form a hermetic seal between the balloon and the casing wall so that water will not leak. Similarly, the other end of the balloon is secured to the tip section 132 so as to form a hermetic seal between the balloon 8 and the tip section. A bulge 134 is provided adjacent the remote end where the balloon 8 is secured to the casing so as to provide an optional marker which can be felt transrectally by the user of the device when the casing is initially inserted into the urethra so as to insure the position of the balloon 8 relative to the prostate gland. In addition radioopaque markers 136 can be optionally provided at opposite ends of the balloon where they are respectively attached to the casing and tip section so that the opposite ends of the balloon 8 can easily be seen fluoroscopically when inserting the balloon into the urethra. The tip section includes a screw drive fitting 138 formed so as to face the interior of the balloon 8 so as to receive the screwdriver configured end of a flexible stylet 140 adapted to function as an insertion guide and shown in place in FIG. 5. The stylet is adapted to extend though and create a seal with the water seal 116 prior to being pushed through the duck bill valve 120 into the casing 18.

As previously mentioned, the balloon 8 is sized so that when inflated to the desired pressure within the prostatic urethra, the urethra of an averaged sized hypertrophied prostate gland will expand so as to compress the tissue by the balloon 8 without necessarily exceeding the elastic limit of the tissue, as such is required in a balloon dilation procedure. An inflated outer balloon diameter of about 12 mm (36F) is adequate for the average sized hypertrophied gland to achieve the compression of the tissue, although this dimension may vary with smaller and larger prostate glands and the balloon may be sized accordingly. The balloon 8 may be made of various known materials already used in other medical procedures, such as those described in U.S. Pat. No. 4,490,421, with polyethylene terephthalate (PET) being preferred for the procedure for the prostatic urethra because of its relatively low modulus of elasticity (and therefore its non-compliant nature) and its transparency to both the laser radiation and ultrasound beam. The material used for the balloon 8 for the prostatic procedure is preferably designed to accommodate approximately two atmospheres (approximately 30 psi) of water pressure and is adapted to hold that pressure for at least five minutes. Preferably, the PET material is designed to rupture if the pressure well exceeds the two atmospheres (e.g., at three atmospheres) in order to insure that ruptures at even greater pressures will not occur causing potential harm to the patient. It should be evident that the material used for the balloon for other procedures in other body passageways may be of a type which is more compliant, such as a latex material, so as to more readily conform to the shape of the passageway, and may operate at other pressures depending upon the balloon size and application.

Finally, as shown in FIG. 4, a pair of small ultrasound transducers 10 and 12 are mounted adjacent one another on the remote end of the shaft 14. The miniature transducers may be any type suitable for the application and may be of the type, for example, described in co-pending application U.S. patent application Ser. No. 151,394 filed Feb. 2, 1988 in the name of Michael A. Martinelli, assigned to the present assignee and now U.S. Pat. No. 4,862,893, issued Sep. 29, 1989. One of the transducers functions as ultrasound transmitter 10 and transmits a beam of radiation at ultrasonic frequencies (e.g., a broad based signal centered at 7.5 MHz) along the axis 144 which is transverse (preferably 90°) to the longitudinal axis of the shaft 14 (and normal to the plane of view shown in FIG. 4) into the area of the prostate of interest. The other transducer positioned adjacent to the transmitter functions as the ultrasound receiver 12 and is adapted to receive ultrasonic echoes reflected from prostatic tissue exposed to the ultrasonic beam produced by the transmitter. The leads provided from the two transducers are indicated at 150, which as previously described extend through the shaft to the pin connectors 88 of the control unit 4. It should be obvious that in some applications a single transducer or an array of transducers can replace the two transducers 10 and 12. In the case of the single transducer, the latter would first function as a transmitter for generating the ultrasonic signal, and then function as a receiver for the returning ultrasonic echoes. As is well known, a standard T/R (transmitter/receiver) switch can be used to switch the transducer between its transmit and reception modes in a manner well known in the art. An ultrasonic window 152 in the sleeve 16 is preferably provided through which the ultrasound beam is transmitted and echoes are received by the two transducers, respectively. The oil provides a good ultrasonic coupling between the transducers and the water disposed in the balloon during the procedure. A reflector 156, reflective of the laser radiation provided by the laser beam delivery system, is positioned relative to the fibers 104 so as to reflect the laser radiation along an axis 158 (normal to the plane of view shown in FIG. 4) parallel and very close to the axis 144 of the ultrasound beam produced by the transmitter 10 (and as a practical matter the two axes are substantially coaxial with one another).

Figure 7:
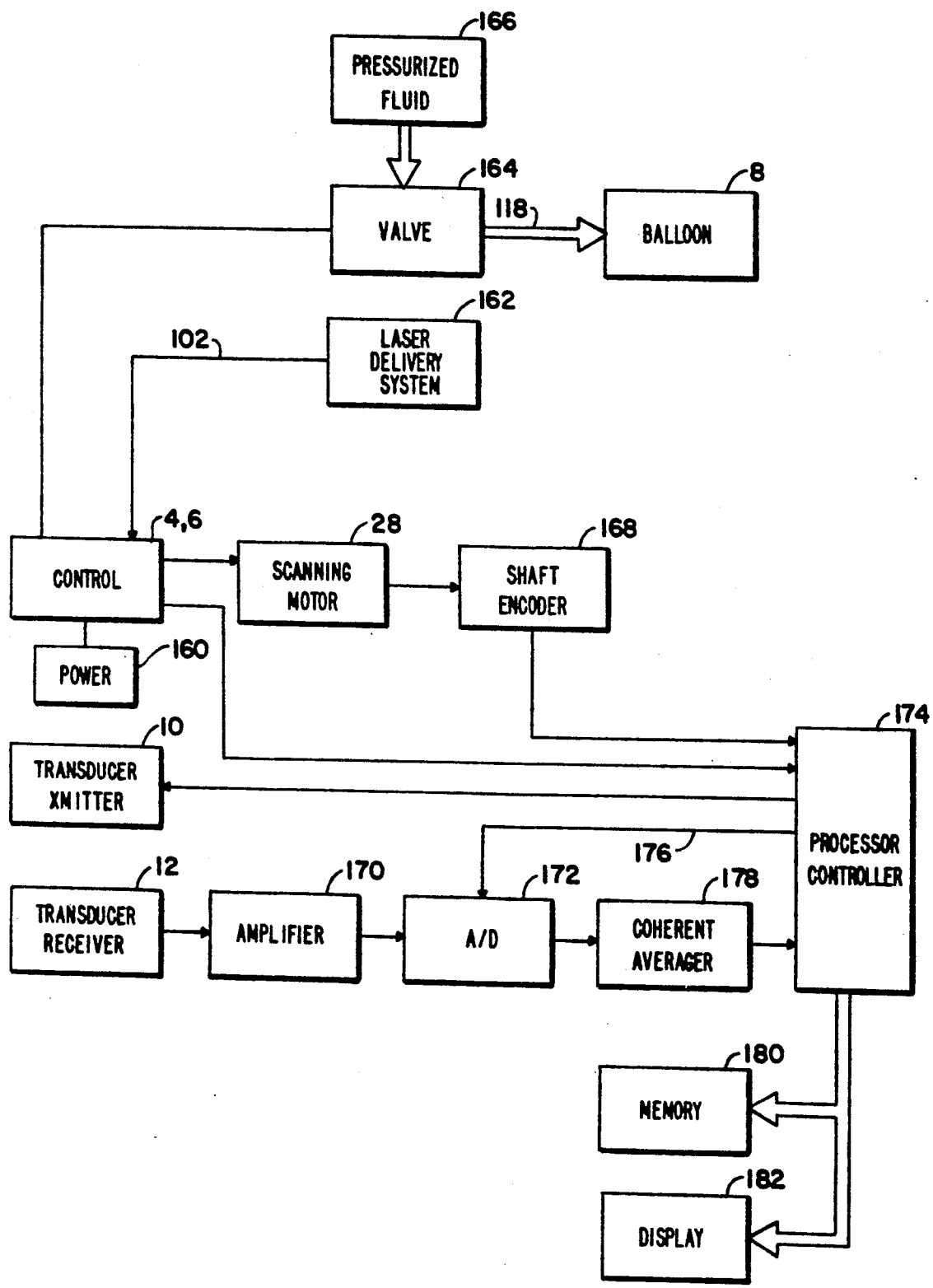
FIG. 7 is a block diagram of the system connected for use.

Referring to FIG. 7, the control unit 4 and catheter unit 6 are appropriately connected to power sources 160. A laser delivery system 162 is connected to the control unit using the connector 102. Preferably, the laser delivery system 162 includes a laser which provides a deeply penetrating continuous wave beam. A preferred example is a 100 watt neodymium-YAG laser because its radiation is not absorbed as strongly by tissue as some other lasers. For example, one such Nd:YAG laser, commercially available from Surgilase, Inc. of Providence, RI as Surgilase model YAG 100, provides continuous wave laser energy at the standard wavelength (for Nd:YAG lasers) at 1.064 micrometers. The laser energy can be delivered through various sized fibers 104, with the diameter of fibers 104 being on the order of 600 micrometers in diameter so as to provide an output laser beam of similar cross-section. The neodymium-YAG laser provides more pronounced scattering with deeper tissue effect occurring. See the Smith et al. and Fisher articles, supra.

A source of pressurized fluid shown at 166 in FIG. 7 is connected to a suitable control valve 164 which is shown as controlled from the unit 4, although it may be separately controlled by the operator. The output of the valve is connected through the water port 118 of the control unit so that fluid can be introduced into the balloon 8.

As the scanning motor 28 rotates the transmitting and receiving transducers 10 and 12 rotate about the axis 38 and scan in a plane containing the axis 158 of the laser beam. Angular resolution depth of view and sweep rate can vary, with a 2 mm angular resolution, 2 to 5 cm adjustable depth of view, and a sweep rate of 2Hz being typical. The angular position of the transducers 10 and 12 and the image information retrieved at each of a plurality of angular positions can be ascertained, processed, stored and displayed. More specifically, the scanning motor 28 includes a shaft encoder 168 for indicating the angular position of the rotor shaft of the motor as the latter rotates about its axis. Control 4 is also connected directly to the processor controller 174 so that the former can be used to provide an actuation signal to the processor controller when the scanning motor is energized by the user.

The rotational position of the rotor shaft is directly related to the pivotal position of the transducers 10 and 12 about the axis 38. The scanning motor 28, when energized, moves the transducers 10 and 12 through a predetermined angle, or continually rotates about the axis 38 in one or either rotational direction as controlled by the operator. The output of the shaft encoder can be a digital signal representative of the angular position of the transducers in finite increments. This output signal is applied directly to the processor controller 174.

The processor controller 174 is also connected to provide signals to the transducer 10 for generating the acoustic signal along the signal generating axis 144 in response to the initiation signal provided by the user. The receiving transducer 12 receives reflected signals from targets substantially along or parallel to the axis 144. Transducer 12 is connected to the input of amplifier 170, which can be positioned on assembly board 58. Amplifier 170 boosts the signals provided by the receiving transducer in response to the reflected acoustic signals. Amplifier 170 is in turn connected to the input of an analog-to-digital (A/D) converter 172 (also provided on the assembly board 58), which converts the analog output of the amplifier 170 to a digital signal. The sampling rate of the A/D converter is provided by processor controller 174 through the control line 176. The digital signal at the output of A/D converter 172 is applied to the coherent averager 178. The latter is provided to average the signals received from the A/D converter since the latter may represent several overlapping reflected signals detected by the receiving transducer 12. The average signal is applied to the processor controller 174. Processor controller 174 correlates the signal provided by the shaft encoder and the signal provided from the coherent averager corresponding to the current pivotal position of the transducer assembly. The two values are then stored in memory 180 and are displayed by the display device 182. Preferably, the values can be displayed as a two dimensional echogram through a predetermined scanning angle (e.g., up to 360°), or alternatively in some matrix arrangement with, for example, the angular position of the transducers about the axis 38 providing one axis of the display and the echogram detected being displayed along the other axis (the latter axis therefore representing distance from the receiving transducer 12 along the axis 144). In this way the data will be spatially correlated with the incremental angular positions of the transducer assembly from which the data was received so as to create a mapped or composite image of the portion of the body viewed during the scanning of the transducer assembly through a slice of the viewed object in a plane normal to the axis 38.

In operation, the instrument thus described is used to carry out the preferred prostatic urethral procedure. More specifically, the linear adjustment assembly 110 which is secured to the outer casing 18 of the catheter unit is fitted with the stylet 142 by inserting the latter into the casing and securing the stylet by securing the end 140 of the stylet into the screw drive fitting 138 in the tip section 132 as best shown in FIG. 5. The stylet will insure that the balloon 8 can be inserted up the urethra into the prostate without folding on itself.

Figure 8:
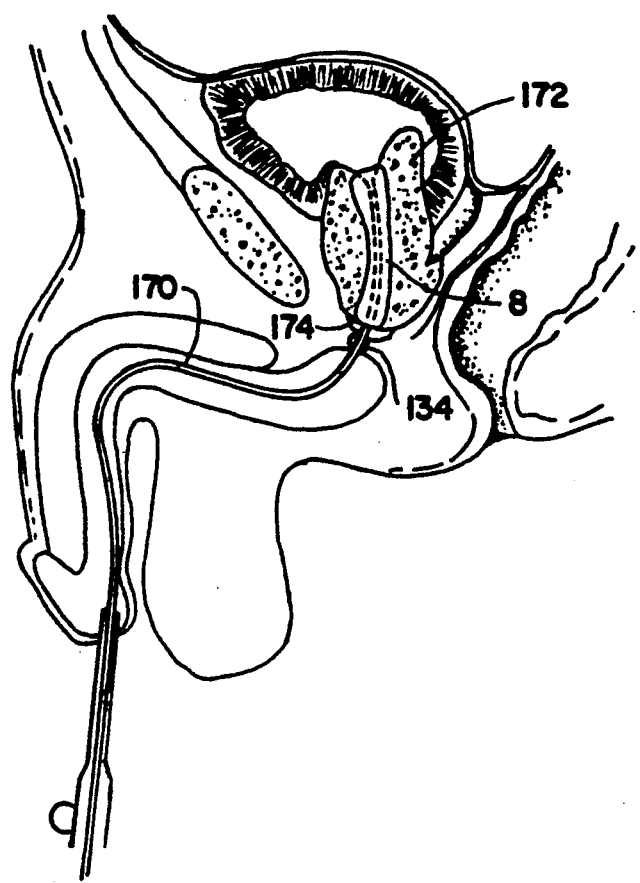
FIG. 8 is an anatomical illustration of the catheter casing and stylet positioned in place so that the balloon is disposed within the prostatic urethra.
Figure 9:
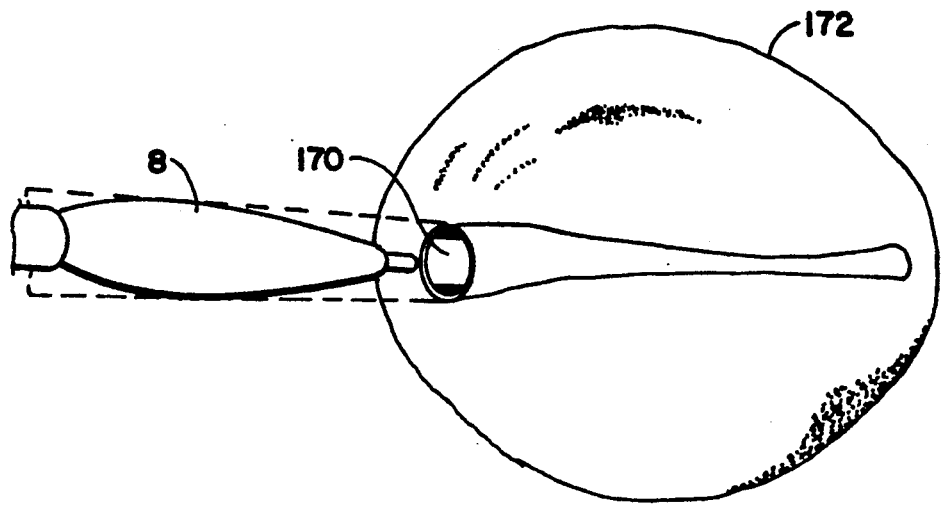
FIG. 9 is an isolated anatomical illustration showing the insertion of the catheter casing and stylet into the prostatic urethra.

The patient is appropriately anesthetized, as for example, with a general or conduction anesthesia. An additional sedative and prophylactic antibiotics can also be given. The penis is then appropriately prepped and draped and the casing with the stylet is inserted through the urethra 170 as illustrated in FIGS. 8, 9 and 10. The clinician can feel the bulge 134 transrectally to insure that the balloon 8 has advanced into the prostatic urethra of prostate 172, past the external sphincter muscle 174, before the balloon is inflated so as to minimize the risk of damage to that muscle when the balloon is inflated. The maneuver can also be observed fluoroscopically by observing the radioopaque markers to insure precise positioning of the balloon 8. Once the balloon is properly positioned pressurized water (at a pressure up to 2 atmospheres) is introduced through the water port 118 so as to fill the casing 18 and inflate the balloon 8 to its maximum diameter as seen best in FIG. 10. Inflating the balloon 8 should compress the prostatic tissue and associated blood vessels so as to improve hemostasis and allow for more uniform laser radiation absorption of the tissue. The substantially non-compliant balloon is sized so that when inflated the resulting shape of the lumen within the prostate is substantially of constant diameter. With the balloon in place, the stylet 140 can be detached from the fitting 138 of the tip section 132 and withdrawn. It will be appreciated that as the stylet is withdrawn it will be pulled through the duck bill valve 120 which will then close before being withdrawn from the water seal 116 so as to substantially maintain the water pressure within the casing 18 and balloon 8.

The shaft and sleeve 14 and 16 are previously secured to the control unit 4 with oil provided through fill port 92 and the transducers fixed in front of the window 152. In addition, the rack gear 122 is already fixed to the nozzle assembly 60, while the pinion gear 124 is previously secured to the housing 112, which in turn is fixed to the casing 18. The probe formed by the shaft and sleeve are threaded through the water seal 116 and through the duck bill valve 120. The latter will permit the entry of the probe, while the seal will prevent significant leakage of the water so that the balloon will remain inflated. The probe can be moved all the way so that the transducers 10 and 12 are disposed within the balloon 8 and the pinion gear 124 engages the rack gear 122. The position of the transducers can be confirmed by viewing the end of the shaft and sleeve fluoroscopically to be sure it is properly positioned between the two radioopaque markers 136.

Exposure of selective tissue of the prostate to the laser beam can now be carried out. Preferably, tissue is exposed to the laser beam at one selected radial angle (preferably 90°) about the longitudinal axis 38 of the shaft 14, while longitudinally moving the shaft along the axis 38. Specifically, the probe formed by shaft 14 and sleeve 16 is moved longitudinally in the casing 18 until the transducers 10 and 12 and reflector 156 are positioned near one end of the prostatic urethra. The laser is energized while simultaneously moving the probe, and therefore transducers and reflector along the longitudinal axis 38 so as to expose tissue receiving the laser energy to a select amount of radiation sufficient to cause general coagulation necrosis of the exposed tissue. Longitudinal movement is achieved by the clinician by rotating the pinion gear 124 so as to move the rack gear 122.

The rate of pull of the probe can vary and is a function of the laser energy exposure, and specifically must be at a rate so as to insure that the tissue does not explode due to the popcorn effect, carbonize or ablate. In particular, with a laser beam spot size of 2.8 millimeters and the laser power set at about 30 watts, if one continuously exposes (i.e., at a zero pull rate) compressed tissue to the laser beam the following sequence of events would occur: (1) the tissue nearest the balloon surface would dehydrate, shortly followed by a (2) popcorn effect or little explosion occurring just below the tissue surface associated with a puff of steam. When water has all been removed form the tissue by the first two steps, a (3) carbonization occurs that causes a blackening of the tissue further increasing the tissue absorption of the laser. Finally, the tissue will (4) ablate, wherein the tissue will actually vaporize. Once the tissue at the front (nearest the balloon) becomes disrupted and carbonized it is a very good absorber of the laser energy and will prevent efficient energy transfer into deep tissue. It takes about five seconds for all four steps of this process to occur when exposing compressed prostatic tissue, although the length of time varies according to the type of tissue and the degree of compression of that tissue. The lesser the degree of compression, the more blood will be present, and the sooner the process will proceed to carbonization. The process can be summarized by saying that for a non-moving laser spot a carbonization "shield" is created in the tissue nearest the balloon. This shield protects the deep tissue from substantial heating by the laser. It is this very effect that has dissuaded most researchers from attempting to treat prostate tissue or other tissue that needs to be treated deeply with a Nd:YAG laser.

By moving the axis of the laser beam laterally over the tissue at a velocity greater than that corresponding to the time for the shield formation, a deep penetration of laser energy occurs. If the spot is laterally moving in the longitudinal direction of the prostatic urethra, for example, at approximately one mm/sec, the spot will have moved to an entirely new location in a time of 2.8 seconds. This is less than the time for formation of the protective shield. Thus, the shield never forms and the energy continues to be conducted deeply into the tissue. Considering two adjacent spots, 2.8 millimeters in diameter, the energy that is put into the first spot will blossom (scatter) out into a mushroom like pattern that ranges to about +/−45° from the direction of incidence of the laser beam normal to the tissue surface, and penetrates deeply to about 0.8 centimeter. The adjacent second spot will therefore have a heavy energy overlap in the deep tissue with the first spot. Hence, the energy will continue to be deposited in the deep tissue as the laser moves from the first to the second spot and give rise to a much higher temperature at the deep tissue without the carbonization or ablation of the tissue at the surface. A range of velocities (pull rates) has been investigated from as low as 0.01 mm/sec to as high as 50 mm/sec. As was stated, about one mm/sec seems to be optimal for the parameters described above, with a spot size of 2.8 mm and 30 watts of power.

It is important to note that the velocity or pull rate need not be uniform (the above parameters refer to average pull rates) so long as steps are taken to avoid over exposure of any particular location to the laser energy. Thus, the same results would occur if the laser beam were moved in staccato fashion in steps of 1 millimeter every second without any motion in the intervening time. Any programmed motion of the spot giving rise to the same average velocity as herein specified is certainly within the realm contemplated for successful operation so long as the average time is less than that required for shield formation at one location.

The selection of spot size and velocity is therefore integrally associated with the kind of tissue that is being exposed and the degree of balloon compression of the tissue and therefore the shield formation time which sets the lower limit on velocity of the spot. Velocities greater than this minimal velocity can be chosen to modulate downward the amount of energy being deposited. Thus, the faster the laser is pulled, the less energy deposited and the lower tissue temperature achieved.

Given a pull rate of 1 mm/sec, for a typical prostate a motion covering about four centimeters is accomplished from the front to the back of the prostate over a period of about 40 seconds. This gives rise at a power level of 30 watts to a total application of about 1200 joules of energy. Tissue at an 8 mm depth will receive energy for 16 seconds as the laser beam passes at 1 mm/sec from +45° to −45° with respect to the angle of incidence of the laser beam. The temperature of the tissue at this selected point will therefore increase during that time period. After the laser has passed, there is a natural cooling by the body and that is estimated to occur within about 30 seconds to one minute after exposure to the laser energy. Thus, the temperature at the selected point will rise for 16 seconds during the application of energy and then drop over a period of 30-60 seconds thereafter. In other words, the total duration of the heating above normal body temperature would range somewhere between 45 seconds to 75 seconds. Experimentations with thermocouples placed in the tissue at the 0.8 centimeter depth has sensed temperature increases to about 70° C. Further, human prostate data has indicated that for a temperature of approximately 70° C., an exposure of about 50 seconds at such a temperature is sufficient to cause coagulative necrosis of the tissue. Higher temperatures (90°-100°) require correspondingly shorter exposure times in order to achieve the same coagulative necrosis effect. Tissue near the balloon surface would fall into this category due to a shorter heating period (2.8 sec) instead of 16 sec (and higher beam intensities) than the deep tissue.

By moving the laser beam longitudinally while exposing the compressed tissue and ultrasonically observing the exposed tissue to determine the onset of dehydration of the irradiated tissue, overheating, and thus tissue ablation is minimized and the popcorn explosion phenomenon is avoided. The inflated balloon moves the surface tissue so as to create a cylindrically shaped lumen of constant diameter with the casing 18 disposed along the axis 38 of the lumen. This insures that the laser beam emanates at a constant distance throughout the length of the dilated lumen, thus insuring a uniform spot size on the surface of the fully dilated prostatic urethra. The spot size is about 2.8 mm when the Surgilase YAG 100 Nd:YAG laser and a 600 micrometer fiber is used with a 36F inflated balloon. Although the power range of the laser can vary depending on the pull rate of the laser beam (which will become more apparent hereinafter), with 20 to 50 watts being typical, a power level of 30 watts is satisfactory. The scanning transducers are used to view the tissue ultrasonically while and after the tissue is exposed in order to determine the area and extent of tissue damage. The ultrasonic image can be viewed on the processor and monitor system 164. If desired this radiation and viewing step of the procedure can be repeated at one or more different angles to the longitudinal axis by manually rotating the transducers and reflector. The laser can then be energized while simultaneously moving the transducers and reflector along the longitudinal axis 38 so as to expose the new tissue receiving the laser energy to a select amount of radiation sufficient to necrose the tissue. The result might be the pattern shown in FIG. 11B, where the necrosed tissue is darkened as indicated at 200. Once all of the selected areas are exposed to the laser radiation, the water pressure can be released at water port 118 so as to deflate the balloon, and the entire instrument withdrawn from the urethra. As soon as the balloon is deflated bodily fluids will flow into the previously compressed and necrosed tissue, without significant bleeding, promoting healing. Over a period of time, the necrosed tissue will slowly slough off as urine is passed through the urinary tract, providing a natural void for the sloughed tissue. During post operative healing large diameter defects within the prostatic urethra are created, causing the internal wall of the urethra to take on a scalloped or similar contour as shown in FIG. 11C and, therefore, relieving outflow obstruction. This effectively results in the post-operative opening of the prostatic urethra.

Animal Studies

Animal studies were performed on dogs identified as appropriate models for human BPH. A total of twenty-one (21) canines were studied, sixteen (16) experimentals and five (5) controls. In the first feasibility experiments, six (6) dogs of various breeds were used but were found to have prostates of inconsistent or insufficient sizes. For the remaining fifteen (15) dogs, the protocol specified fox hounds more than five (5) years of age and weighing an average of 25 kg. The prostates of these animals were between 3 and 4 cm in diameter and 20 to 25 mm in prostatic urethral length and weighed between about 22 and 29 gm. While BPH in canines is not the exact homologue of human BPH, it is an acceptable experimental model.

A prototype device of the type of system claimed herein was built and used in all of the experiments. The prototype device was used with a Surgilase YAG 100 laser, identified above. Although the initial ultrasound imaging system was unsatisfactory, as described below, the final ultrasound system operated at 7.5 MHz providing a 90° sector scan, 4.5 cm range and 2 mm spatial resolution. The laser delivery system utilized a 600 micron fused silica fiber, with a 2.8 mm spot size in tissue as described above. In addition, as described below two different sized balloons were utilized, a 22F by 5 cm inflatable, substantially non-compliant balloon, and a 36F by 5 cm inflatable, substantially non-compliant balloon.

The system used for each animal test was verified using a laser power meter and ultrasound phantom image. The fluid controller utilized a sterile pressure pump and the balloon was inflated with a balloon water pressure between one and two atmospheres.

The anatomy of the urethra of a male dog is different from a human male in that the dog's urethra has a sharper bend than in the human; the prostate is spaced from the bladder with an interconnecting urethral section, while the human prostate is attached directly to the neck of the bladder, and the cross-sectional diameter of the normal, average sized urethra of a dog is smaller than the corresponding average, normal human prostatic urethra. Accordingly, a perineal urethrostomy was first performed on each dog to avoid the sharp natural bend in the urethra which would not be necessary in humans. The urethra of the dog needed to be initially dilated which would also not be necessary for humans. This initial dilation was performed to a size 28F.

The probe of the device including the inflatable balloon was passed into the prostatic urethra and a videocystoscope was used to view and record the image of the interior of the prostatic urethra. The balloon was inflated to a pressure of one to two atmospheres. The ultrasound system was used to determine the various landmarks including the bladder neck and the apex of the prostate, as well as the thickness of the prostate.

The tissue was first compressed by inflating the balloon. The laser beam was then used to radiate in a normal direction to the axis of the probe in a radial direction into the prostate tissue. The device was operated so as to pull the laser beam in an axial direction between bladder neck and apex of the prostate. The pull times varied from 15 to 56 seconds per pass. The power was varied between 20 and 55 watts. 1-11 lesions per prostate gland were made with the laser. The balloon was maintained stable while moving the laser ultrasound system within the balloon.

The interior of the prostate was then videocystoscoped in order to record the gross surface changes. No significant acute tissue removal was noted. No post operative catheter was utilized. Each animal was euthanized between 6 hours and 11.5 weeks following exposure. The prostate tissue was fixed in 10 percent formaline solution. The tissue was then processed routinely and stained with Hematoxylin and eosin, and Masson's trichrome stain.

Initial results, however, were not satisfactory since the ultrasound system was inadequate in providing a good image of the prostate tissue exposed to the laser radiation. In fact the laser beam perforated the urethral tissue between the prostate and the bladder of the first two dogs before it was realized that the dogs' anatomy was different from the human anatomy, as described above. As a result of these initial experiments the ultrasound imaging system was improved so as to provide greater imaging resolution within the prostate, and therefore greater control of the direction and power usage of the laser beam was achieved.

Table 1 indicates the ranges of power used to create necrosis lesions and the corresponding tissue penetration.

TABLE 1

| Power (W) | No. of Lesions | Average Energy (Joules) | Average Length of Lesion (mm) | Average Depth of of Tissue Loss after Healing (range, mm) |
|---|---|---|---|---|
| 20 | 10 | 463 | 21 | 8.2 (5.5–9.0) |
| 30 | 1 | 1672 | 16 | 6.0 |
| 40 | 11 | 957 | 21 | 8.7 (5.0–10.5) |
| 50 | 3 | 1437 | 20 | 7.4 (5.0–8.0) |

Table 2 indicates coagulation necrosis of the tissue over time.

TABLE 2

| Range of Time | Coagulation Necrosis | Hemorrhage | Peripheral Glandular Atrophy | Tissue Sloughing | Reepithelialization |
|---|---|---|---|---|---|
| 6h-5d | ++++ | 0 | + | ++ | 0 |
| 6-14d | +++ | 0 | ++ | +++ | ++ |
| 15-25d | + | 0 | +++ | + | +++ |
| 26-73d | 0 | 0 | +++ | 0 | ++++ |

As indicted in TABLE 2 there is atrophy, i.e. a decrease in glandular tissue over time. The bulk of the tissue was lost through urination between 6 hours and 14 days and the loss was complete by approximately three to four weeks. As indicated under the column "Reepithelialization" of Table 2 there was a reoccurrence of the inner lining of the prostate urethra as the tissue healed. A complete urothelial lining occurred at the latest six weeks after treatment.

The histological specimens revealed a trend that the greater the application of laser power applied to the tissue the greater the depth of the necrosed lesion.

A comparison was made between a treated atrophic prostate and a normal prostatic gland suggesting a reduction in the bulk of the tissue which had been treated. In addition to the foregoing test, additional tests were made on 4 dogs in which the size of the balloon was the only variable, a 22F shaft and a 36F balloon were used. Based on this study, the larger balloon, causing greater compression of the tissue, provided for deeper penetration by the laser and greater tissue atrophy with the application of the same laser energy.

CONCLUSION

The foregoing instrument and surgical technique are believed to provide several advantages in the treatment of symptoms of BPH. It is believed that the procedure will substantially reduce the length, dangers and degree of post-operative care currently required for the TURP procedure since it is currently estimated that the entire procedure described herein can be carried out on an out-patient basis or require hospital care on a single overnight basis. Further, by damaging the tissue with the laser so as to cause selective general, coagulation necrosis in predetermined areas of the prostate it is believed that the procedure will substantially eliminate post-operative bleeding and trauma. The necrosed tissue slowly sloughs off and is voided by natural body fluids passing through the urinary tract eliminating one of the needs for fluid irrigation. Further, with the use of ultrasound the need for a clear optical view within the lumen during the procedure is no longer required, thus, eliminating the other reason for fluid irrigation. Eliminating the need for fluid irrigation during the procedure eliminates the risks associated with fluid overload. It is believed that the procedure will reduce the chances of tissue damage associated with impotence and muscle damage associated with incontinence since the direction and penetration of the laser energy can be carefully viewed and controlled. The entire procedure is performed without the need of hormonal treatments or long term heat therapy. Further, by inflating the balloon sufficiently to squeeze the tissue so as to compress the tissue without necessarily exceeding its elastic limit, the tissue will not be unnecessarily damaged due to tearing. Finally, the ultrasound transmitter and receiver 10 and 12 are positioned transurethrally so as to make the procedure much more controllable because of the proximity of the transducers to the tissue and the ability of the clinician to view the area and depth of the tissue being exposed to the laser radiation in real time.

It should be evident that while the preferred embodiment of the method and instrument have been described for use in transurethral prostatic surgery for reducing the symptoms of BPH, the present invention can be used to treat any type of tissue, such as tumors, as well as used in other parts of the body. For example, the instrument can be used for removing tumors found in the prostate because such tumors are usually identifiable ultrasonically. The balloon can be used to compress the tumor and the laser beam can be subsequently used to cause coagulation necrosis of the tissue of the tumor. The instrument and technique can be used in other parts of the body for treating tissue such as hemorrhoids. In the latter situation the hemorrhoids would be compressed so as to force blood from the hemorrhoidal tissue and so as to make the tissue more hemostatic as well as provide more uniform absorption of the laser energy. The hemorrhoidal tissue can then be necrosed by the laser beam. In this application the balloon used should be preferably more compliant than the type used in the prostatic procedure described above.

Since certain changes may be made in the above apparatus and process without departing from the scope of the invention herein involved, it is intended that all matter contained in the above description or shown in the accompanying drawing shall be interpreted in an illustrative and not in a limiting sense.

What is claimed is:

1. An instrument for use in effectively removing anatomical constrictions of the prostatic urethra, the instrument comprising:

a catheter casing sufficiently long so that a portion of the casing can be inserted into the prostatic urethra within the anatomical constrictions;

an inflatable balloon, substantially transparent to selected laser radiation and supported on the portion of the catheter casing so that the balloon is insertable into the prostatic urethra within said anatomical constrictions, the balloon being size so that when inflated within the prostatic urethra the balloon assumes a substantially fixed and uniform cross-sectional dimension so as to reconfigure at least a selected part of the tissue of the urethra into a smooth uniform cylindrical shape having an axial direction such that a corresponding portion of the prostate is squeezed from within the urethra and balloon excluding means for comprising the tissue and associated blood vessels of the corresponding portion of the prostate so as to decrease blood flow and promote hemostasis in the tissue, and means for providing for uniformity and increased depth of penetration of said selected laser radiation in the corresponding portion of the prostate;

a probe axially and rotatably movable within the casing and the balloon;

means, fixed relative to said probe, for transmitting a beam of said selected laser radiation in a direction transverse to said axial direction through the balloon into at least a volumetric portion of the tissue compressed by the balloon where an anatomical constriction exists;

a control unit, coupled to said catheter casing and said probe, including means for setting a rotational position of said probe so as to set the transverse direction of the beam of laser radiation relative to said balloon when compressed tissue is exposed to said beam of radiation, and means for moving the probe within and relative to the casing and balloon along the prostatic urethra so as to move said means for transmitting said beam of laser radiation relative to said balloon while transmitting said beam of said selected laser radiation through the balloon directly into at least a portion of the tissue compressed by the balloon; and means, fixed relative to said probe and movable relative to said casing and balloon, for ultrasonically observing said volumetric portion of said tissue as the tissue is exposed to the beam of laser radiation.

2. An instrument according to claim 1, further including means for transporting liquid within said casing to said balloon for inflating said balloon and maintaining said balloon in an inflated state with said liquid.

3. An instrument according to claim 1 wherein said tissue has an elastic limit and said balloon is sized so that when inflated within said prostatic urethra, the pressure on said tissue will not exceed the elastic limit of the tissue of an averaged sized hyperplastic prostate gland.

4. An instrument according to claim 1, wherein said means for transmitting said beam of selected radiation includes fiber optic means, fixed relative to said probe, for directly transmitting said beam through said casing to said balloon, and reflector means for reflecting said beam at a transverse angle to said elongated direction of said prostatic urethra, said reflector means being positioned on said probe relative to the inflated balloon so as to reflect said beam from a location at equal distances to the wall of the selected part of the urethra reconfigured by said inflated balloon regardless of the rotational position of said probe when compressed tissue is exposed to said beam of radiation.

5. An instrument according to claim 4, wherein said means for ultrasonically observing said volumetric portions of said tissue includes transducer means positioned adjacent to and movable with said reflector means for transmitting an ultrasonic beam into said tissue and transducer means for receiving reflections of said ultrasonic beam from said tissue.

6. An instrument according to claim 5, wherein said transducer means includes a pair of transducers fixedly secured relative to said probe and said reflector means includes a reflector fixedly secured relative to said transducers.

7. An instrument according to claim 1, wherein said control unit includes means for moving said probe axially within and relative to the casing and balloon along the prostatic urethra at a controllable rate so as to move said means for transmitting said beam of laser radiation relative to said inflated balloon while transmitting said beam of said selected laser radiation through the balloon.

8. An instrument according to claim 7, wherein said means for moving said probe at said controllable rate is operated so that said beam of laser radiation transmitted directly into at least a volumetric portion of the tissue compressed by the inflated balloon is of sufficient power at a predetermined and constant spot size and of sufficient duration to cause coagulation necrosis of said irradiated tissue portion after said tissue is exposed to said beam of laser radiation so that as said tissue portion heals the treated and thus coagulated tissue is expelled through the urethra over time and the anatomical constriction of the prostatic urethra post-operatively effectively opens.

9. An instrument according to claim 8, wherein said means for ultrasonically observing said volumetric portion of said tissue includes means for observing said tissue prior to the exposure of said tissue to said beam of laser radiation so that the controllable rate can be determined.

10. A method of effectively removing one or more anatomical constrictions of a prostatic urethra and relieve the signs and symptoms associated with such constrictions, said method including the steps of:
inserting a portion of an instrument including an inflatable balloon which is transparent to selected radiation into the prostatic urethra so that the boon is positioned within at least a selected part of the prostatic urethra including at least one anatomical construction;
inflating the balloon so that at least a selected part of said prostate is compressed from within the anatomical constriction so as to (a) compress the tissue and associated blood vessels of the selected part so as to decrease the flow of blood in the tissue and promote hemostasis, and (b) provide for uniformity and increased depth of penetration of the selected laser radiation into the selected part of the prostate;
moving a beam of said selected laser radiation from within the prostatic urethra and balloon, in a direction relative to the compressed tissue, so as to irradiate one or more selected portions of the compressed tissue and associated blood vessels of the prostate at said constriction so that coagulation necrosis of selected portions of the prostate is caused by the laser irradiation, ultimately resulting in treated tissue being expelled through the urethra, which is turn results in an increase of cross-sectional dimensions of the prostatic urethra; and
ultrasonically observing the selected portions of the tissue and associated blood vessel forming said prostatic urethra in order to control the amount of irradiation of said tissue by said laser means.

11. A method according to claim 10, where said step of moving said laser beam includes the step of moving the laser beam relative to the balloon at a rate so that each selected portion of said tissue exposed to said laser radiation absorbs controlled levels of said radiation per unit volume of tissue.

12. A method according to claim 10, wherein said step of moving the laser beam includes the step of transmitting the beam along a transmission axis into each selected portion of the compressed tissue from the same uniformly spaced distance from the wall of said prostatic urethra.

13. A method according to claim 10, wherein said step of ultrasonically observing said tissue includes the step of ultrasonically observing said tissue before, during and after said irradiating step.

14. A method according to claim 10, wherein said step of ultrasonically observing said tissue from within said urethra includes the step of moving said beam of radiation substantially coincident with and relatively fixed with respect to said direction of ultrasonic observation during said irradiating step.

15. A method according to claim 10, further including the step of ultrasonically observing the selected portions of the tissue and associated blood vessels forming the prostatic urethra in order to allow for quantification and characterization of said tissue and determine the distance of the beam of radiation from the observed tissue.

16. A method according to claim 10, further including the step of setting the direction of the laser beam at a predetermined angle to a longitudinal direction of the prostatic urethra at which the laser beam is moved along the prostatic urethra relative to the balloon when irradiating a selected portion of the compressed tissue.

17. A method according to claim 16, further including the steps of setting the angle of the direction of the laser beam about the longitudinal direction of the prostatic urethra at each of a plurality of predetermined angles and moving the laser beam from within the prostatic urethra relative to the balloon and the compressed tissue at each of the predetermined angles.

* * * * *

UNITED STATES PATENT AND TRADEMARK OFFICE
CERTIFICATE OF CORRECTION

PATENT NO. : 5,207,672

DATED : May 4, 1993

INVENTOR(S) : Robert A. Roth and Michael A. Martinelli

It is certified that error appears in the above-identified patent and that said Letters Patent is hereby corrected as shown below:

Claim 1, col. 20, line 25, delete "size" and substitute therefor -- sized --;

Claim 1, col. 20, line 32, delete "and" and substitute therefor -- ,said --;

Claim 1, col. 20, line 33, delete "excluding" and substitute therefor -- including (a) --;

Claim 1, col. 20, line 33, delete "comprising" and substitute therefor -- compressing --;

Claim 1, col. 20, line 36, after the second "and" insert -- (b) --;

Claim 10, col. 21, line 67, delete "boon" and substitute therefor -- balloon --;

Claim 10, col. 22, line 2, delete "construction" and substitute therefor -- constriction --;

Claim 10, col. 22, line 5, after "compress" delete -- the --;

Claim 10, col. 22, line 20, delete "is" and substitute therefor -- in --;

Claim 10, col. 22, line 25, delete "means" and substitute therefor -- beam --.

Signed and Sealed this

First Day of November, 1994

*Attest:*

BRUCE LEHMAN

*Attesting Officer*   *Commissioner of Patents and Trademarks*